United States Patent
Shemesh et al.

(10) Patent No.: US 10,347,462 B2
(45) Date of Patent: Jul. 9, 2019

(54) IMAGING OF CRYSTALLINE DEFECTS

(71) Applicant: Applied Materials Israel Ltd., Rehovot (IL)

(72) Inventors: Dror Shemesh, Hod Hasharon (IL); Uri Lev, Mazkeret Batya (IL); Benjamin Colombeau, San Jose, CA (US); Amir Wachs, Caesarea (IL); Kourosh Nafisi, San Jose, CA (US)

(73) Assignee: Applied Materials Israel Ltd., Rehovot (IL)

( * ) Notice: Subject to any disclaimer, the term of this patent is extended or adjusted under 35 U.S.C. 154(b) by 0 days.

(21) Appl. No.: 15/955,467

(22) Filed: Apr. 17, 2018

(65) Prior Publication Data
US 2019/0180975 A1    Jun. 13, 2019

Related U.S. Application Data

(60) Provisional application No. 62/597,083, filed on Dec. 11, 2017.

(51) Int. Cl.
| | |
|---|---|
| *H01J 37/22* | (2006.01) |
| *H01J 37/28* | (2006.01) |
| *H01J 37/244* | (2006.01) |

(52) U.S. Cl.
CPC .......... *H01J 37/222* (2013.01); *H01J 37/244* (2013.01); *H01J 37/28* (2013.01);
(Continued)

(58) Field of Classification Search
CPC ........ H01J 37/222; H01J 37/244; H01J 37/28; H01J 2237/221; H01J 2237/24475; H01J 2237/2804; H01J 2237/2813
See application file for complete search history.

(56) References Cited

U.S. PATENT DOCUMENTS 5,576,543 A * 11/1996 Dingley ............... H01J 37/26
                                          250/311
6,326,619 B1 * 12/2001 Michael .............. H01J 37/2955
                                          250/307
(Continued)

OTHER PUBLICATIONS

Naresh-Kumar, G. et al., "Electron channeling contrast imaging studies of nonpolar nitrides using a scanning electron microscope," Appl. Phys. Lett., 102, 142103 (2013), 5 pages.
(Continued)

*Primary Examiner* — David E Smith
(74) *Attorney, Agent, or Firm* — Kilpatrick Townsend & Stockton LLP

(57) ABSTRACT

A method for detecting crystal defects includes scanning a first FOV on a first sample using a charged particle beam with a plurality of different tilt angles. BSE emitted from the first sample are detected and a first image of the first FOV is created. A first area within the first image is identified where signals from the BSE are lower than other areas of the first image. A second FOV on a second sample is scanned using approximately the same tilt angles or deflections as those used to scan the first area. The BSE emitted from the second sample are detected and a second image of the second FOV is created. Crystal defects within the second sample are identified by identifying areas within the second image where signals from the BSE are different than other areas of the second image.

20 Claims, 12 Drawing Sheets

(52) U.S. Cl.
 CPC ............... *H01J 2237/221* (2013.01); *H01J 2237/24475* (2013.01); *H01J 2237/2804* (2013.01); *H01J 2237/2813* (2013.01)

(56) References Cited

U.S. PATENT DOCUMENTS

2007/0120054 A1* 5/2007 Yoon .................... G01N 23/203
 250/307
2017/0365441 A1* 12/2017 Bedell .................. G01N 23/207

OTHER PUBLICATIONS

Zaefferer, S. et al., "Theory and application of electron channelling contrast imaging under controlled diffraction conditions," ScienceDirect, No. 154, Acta Materialia 75 (2014) 20-50, 31 pages.

\* cited by examiner

IMAGING OF CRYSTALLINE DEFECTS

CROSS REFERENCE TO RELATED APPLICATIONS

This application claims the benefit of U.S. Provisional Application No. 62/597,083, filed Dec. 11, 2017, the contents of which are incorporated herein by reference in their entirety for all purposes.

BACKGROUND

All crystalline materials have some level of defects. There are a number of different types of crystal defects, and they are generally categorized as either point defects, linear defects, or planar defects. Point defects are typically places where an atom is missing or irregularly placed in a crystalline structure. Linear defects are typically groups of atoms in irregular positions in the structure. Planar defects are typically interfaces between homogeneous regions of the material.

Crystalline materials are used in a number of different manufacturing processes. Depending on the process and intended application, they are typically used because of some beneficial property of the material. As an example, crystalline silicon materials are used in producing semiconductor devices because conductivity of the material can be controlled based on a concentration of impurity atoms in the material. A number of other crystalline materials are used in semiconductor or other device or material processing operations.

Because crystalline materials are typically used to exploit some particular property of the material, it is generally important to control characteristics of the material to ensure the particular property is provided within some threshold limits. Some characteristics that may be controlled include impurity levels and defect concentrations. These characteristics may affect the particular property directly or may have some other undesirable consequence. For example, crystalline defects in semiconductor devices may not have a significant effect on bulk conductivity, but they may be the source of leakage current that renders the device inoperable. Generally, there is a correlation between crystalline defect concentration and yield or performance of semiconductor devices, especially in microprocessor devices, dynamic random-access memory (DRAM) devices, static random-access memory (SRAM) devices, complementary metal-oxide semiconductor (CMOS) imaging devices, and other devices.

The primary methods for identifying crystal defects are destructive cross-sectional or plan view imaging techniques (e.g., using transmission electron microscopy, secondary electron microscopy, and the like). Oftentimes defects in semiconductor processing are not identified until a device fails end-of-line (EOL) at electrical or yield testing. Thus there may be a delay of weeks or even months between a crystal formation process and analysis identifying a crystal defect as a culprit for device failure or performance degradation.

Besides being destructive, conventional imaging techniques are too slow to allow in-line defect monitoring. Also, the amount of data that can be practically produced is too small to satisfy the need. The probability of a cross-section intersecting a point or linear crystal defect is low. Further, depending on the plane, crystal defects may not be visible even if captured in a cross-section or plan view image. It is estimated that sensitivity of cross-sectional and plan view imaging techniques to crystal defects is several orders of magnitude lower than what is needed for proper process control. Thus, there is a need for improved methods for detecting defects in crystalline materials.

SUMMARY

Embodiments described herein enable nondestructive and near real-time methods for detecting defects in crystalline materials with improved sensitivity compared to conventional techniques. In an embodiment, for example, a charged particle beam apparatus, such as a scanning electron microscope (SEM), may be used to scan a crystalline material. A large field of view (FOV) of the crystalline material is scanned using a number of different tilt and azimuth angles (collectively referred to herein as tilt angles). A first image is formed using back scattered electrons (BSE) emitted from the material, and a first area within the first image is identified where signals from the BSE are lower than other areas of the first image. A small FOV of the crystalline material is then scanned using a charged particle beam with substantially the same tilt angles that were used to scan the first area within the first image. A second image is formed and crystalline defects are identified where signals from the BSE are different (e.g., higher or lower) than other areas of the second image.

The first area in the first image where signals from the BSE are lower than other areas of the first image corresponds to an area where the tilt angles of the charged particle beam are substantially aligned with the crystal orientation of the material. Using these tilt angles, the charged particle beam is more likely to travel through the crystalline material with fewer collisions. A smaller FOV of the crystalline material is then scanned using the same tilt and azimuth angles that were used to scan the first area within the first image. Because these tilt angles are substantially aligned with the crystal orientation, the signals from BSE within the smaller FOV will generally be low. The areas within the smaller FOV with crystal defects will have different signals from BSE (e.g., higher or lower) thus allowing the defects to be detected.

Embodiments are also directed to apparatuses for carrying out the disclosed methods and include apparatus parts for performing each described method feature. The method features may be performed by way of hardware components, a computer programmed by appropriate software, by any combination of the two, or in any other manner. Furthermore, embodiments are also directed to methods of operating the described apparatuses and include method features for carrying out every function of the apparatuses.

In accordance with an embodiment, a method for detecting defects in a crystalline material using a charged particle beam apparatus includes scanning a first sample of the crystalline material using a charged particle beam. A first FOV of the charged particle beam covers an area on the first sample of the crystalline material, and a plurality of different tilt angles of the charged particle beam are used to scan the first FOV. BSE emitted from the first sample of the crystalline material are detected using one or more detectors of the charged particle beam apparatus. A first image of the first FOV is created based on the detected BSE, and a first area within the first image is identified where signals from the BSE are lower than other areas of the first image. Tilt angles of the charged particle beam used to scan the first area are determined. A second sample of the crystalline material is scanned using the charged particle beam. The second sample has a crystalline orientation relative to the charged particle beam apparatus that is substantially the same as the first sample. A second FOV of the charged particle beam covers an area on the second sample of the crystalline material that is smaller than the first FOV, and the charged particle beam has approximately the same tilt angles as those used to scan the first area. The BSE emitted from the second sample of the crystalline material are detected using the one or more detectors of the charged particle beam apparatus, and a second image of the second FOV is created based on the detected BSE. Crystal defects within the second sample of the crystalline material are identified by identifying areas within the second image where signals from the BSE are different than other areas of the second image.

In accordance with another embodiment, a charged particle beam apparatus includes a controller configured to scan an area of a sample multiple times using different tilt angles that are each substantially aligned with a crystal orientation of the sample. This can be achieved, in some embodiments, by performing overlapping scans where the overlapping areas are scanned using different tilt angles.

In accordance with yet another embodiment, a charged particle beam apparatus includes a controller configured to utilize automatic defect review (ADR) to automatically detect crystal defects in accordance with other embodiments described herein. The controller may also be configured to automatically count and/or classify the crystal defects. Results such as counts, densities, or the like can be provided based on FOV, area, structure, location, die, and/or wafer.

Numerous benefits are achieved using embodiments described herein over conventional techniques. For example, some embodiments provide nondestructive methods for detecting crystal defects. Crystalline materials can be analyzed immediately after formation thus providing near real-time feedback for process control. Some embodiments can also provide improved sensitivity for detecting crystal defects compared to conventional techniques. As an example, results have shown that crystal defect sensitivity can be improved by orders of magnitude over cross-sectional or plan view TEM analysis. Some embodiments can also provide large amounts of data in a relatively short amount of time. This allows for improved process control.

Further aspects, advantages, and features will be apparent from the claims, description, and accompanying drawings.

Figure 1:
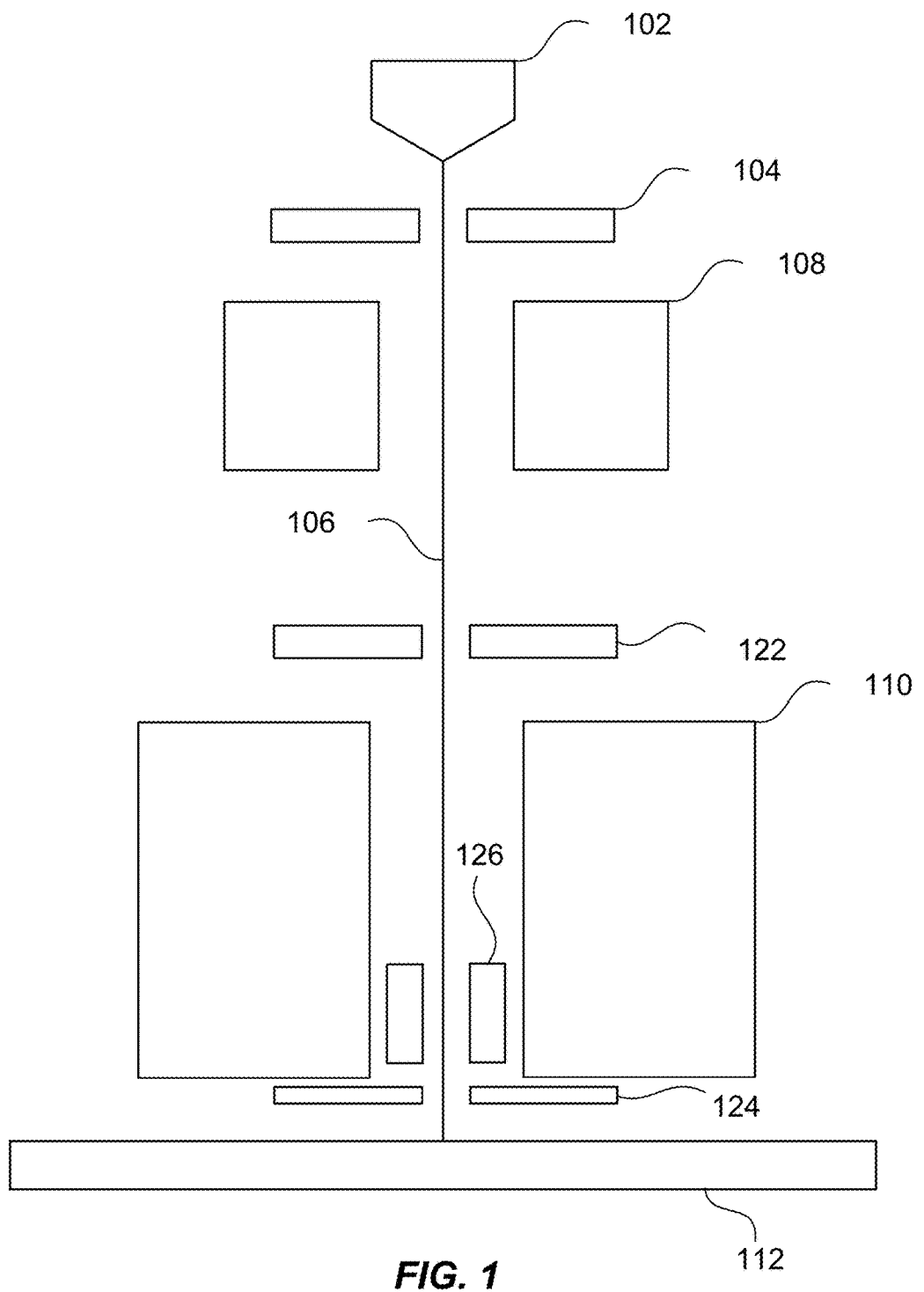
FIG. 1 is a simplified cross-sectional view of an exemplary charged particle beam apparatus that may be used to implement some embodiments described herein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the embodiments described herein. However, it should be understood that the various embodiments can be practiced without these specific details. In other instances, well-known methods, procedures, and components have not been described in detail so as not to obscure the described features.

Reference will be made in detail to the various embodiments, one or more examples of which are illustrated in the figures. Each example is provided by way of explanation and is not meant as a limitation. Further, features illustrated or described as part of one embodiment can be used on or in conjunction with other embodiments to yield yet further embodiments. The description is intended to include these modifications and variations.

Any reference in the specification to a method should be applied mutatis mutandis to a system capable of executing the method as well as a nontransitory computer-readable medium storing instructions that, when executed by one or more processors, result in execution of at least a portion of the method.

Any reference in the specification to a system should be applied mutatis mutandis to a method that can be executed by the system as well as a nontransitory computer-readable medium storing instructions that may be executed by the system.

The following text includes various examples that refer to a scanning electron microscope (SEM) for generating BSE. It should be noted that a SEM is a non-limiting example of a charged particle beam apparatus. The charges particles may be electrons or ions. Other examples of charged particle beam apparatuses include a transmission electron microscope (TEM), a scanning transmission electron microscope (STEM), and the like.

Embodiments described herein provide nondestructive systems and methods for detecting defects in crystalline materials. In an embodiment, for example, a charged particle beam apparatus may be used to scan a crystalline material using a number of different tilt angles. Each tilt angle aligns differently with the crystal orientation of the crystalline material. Tilt angles that do not align with the crystal orientation have higher signals from BSE. Tilt angles that do align with the crystal orientation have lower signals from BSE. Defects in the crystalline material can be detected by scanning the crystalline material using tilt angles of the charged particle beam that align or substantially align with the crystalline material.

FIG. 1 is a simplified cross-section view of an exemplary charged particle beam apparatus that may be used to implement some embodiments described herein. This charged particle beam apparatus is provided merely as an example. The methods described herein may be implemented using other charged particle beam apparatuses that may or may not include the same or similar features.

In this example, a charged particle source 102 is provided to generate charged particles that are accelerated by an electrode 104 to form a charged particle beam 106. As an example, the source may generate electrons that are accelerated by the electrode 104 to generate an electron beam.

The apparatus in this example includes a condenser lens 108 and an objective lens 110. The objective lens 110 focuses the charged particle beam 106 onto a spot on sample 112 using known focusing techniques. The condenser lens 108 and the objective lens 110 may use magnetic and/or electrostatic elements.

The apparatus also includes deflectors 124, 126. These deflectors may form or be part of a deflection system that is configured to deflect the beam 106 for scanning an area of the sample 112.

The apparatus also includes a detector 122 for detecting charged particles emitted and/or reflected from the sample 112. The detector 122 is not limited to the configuration shown in this example and may be disposed before the objective lens 110, after the objective lens 110, or within the objective lens 110. Some embodiments may include multi-detector configurations.

The detector 122 may be configured in accordance with known techniques to detect a number of different types of charged particles including secondary electrons (SE) and BSE. In some embodiments, charged particles that are not of interest may be filtered out before reaching the detector 122 or their signals may be filtered out by the detector 122. Alternatively, the detector 122 may be configured to detect only a particular type or types of charged particles (e.g., SE and/or BSE).

Although not specifically shown in this example, the apparatus may be configured to tilt the beam 106 relative to the sample either electronically and/or mechanically in accordance with known techniques. For example, the beam 106 may be tilted electronically using a deflection system that may include magnetic and/or electrostatic elements such as deflectors 124, 126. The beam may also be tilted mechanically by tilting a stage that supports the sample 112 and/or by tilting the column relative to the sample 112. The beam 106 may be tilted electronically by angles as high as 15° or more using known techniques. The beam 106 may be tilted mechanically by even larger angles.

Figure 2:
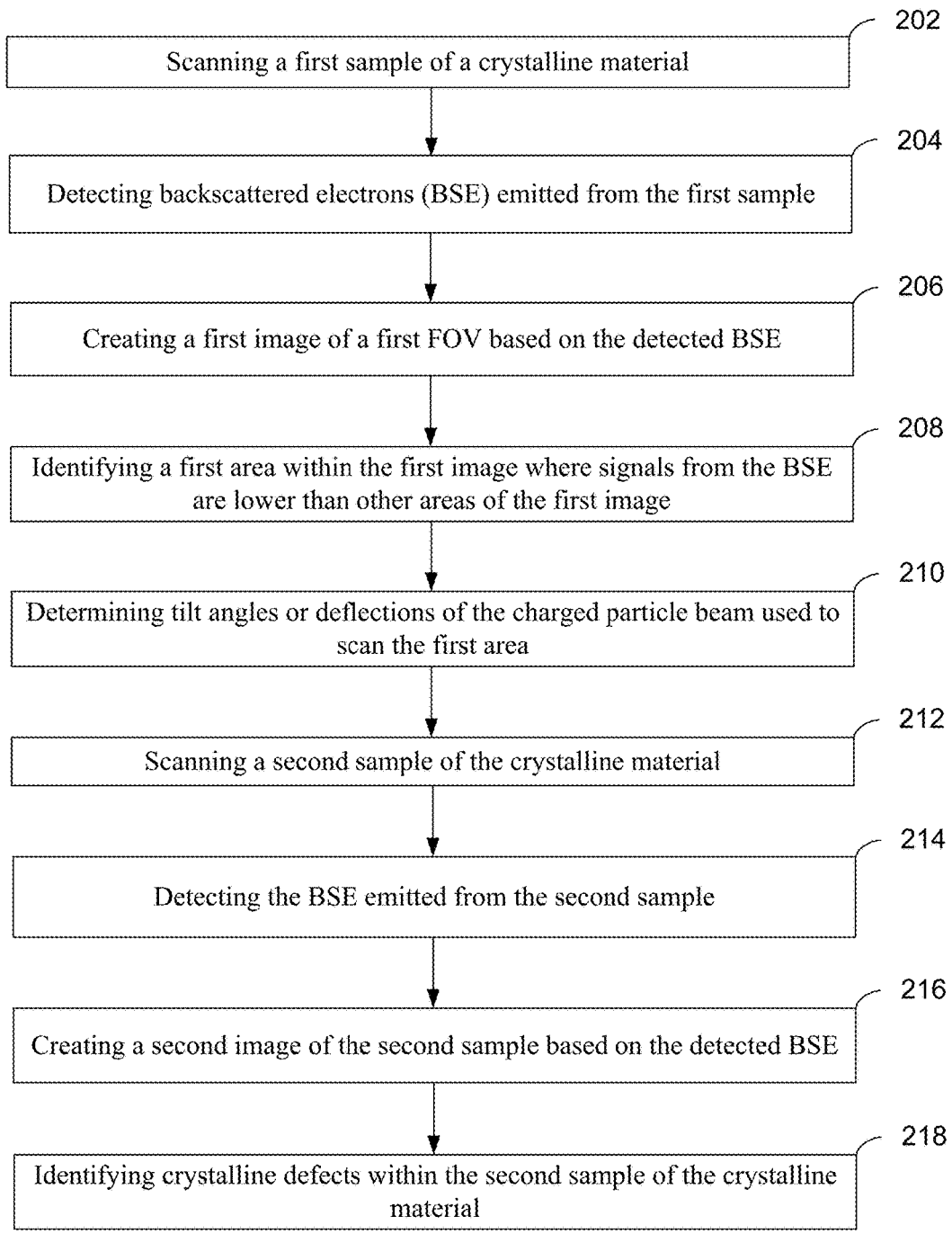
FIG. 2 is a flowchart of a method for detecting defects in a crystalline material in accordance with an embodiment.

FIG. 2 is a flowchart of a method for detecting defects in a crystalline material in accordance with an embodiment. The method involves scanning a first sample of a crystalline material (202). The first sample is scanned using a charged particle beam of a charged particle beam apparatus. The charged particle beam may be an electron beam of a SEM. In some embodiments, a tilt angle of the charged particle beam is increased with distance from a center of a first FOV. This provides for a number of different tilt angles to be used during the scan.

In accordance with an embodiment, the scan is a two dimensional scan that changes on two axes (e.g., X and Y axes). Therefore, the same tilt can be obtained with different azimuth angles. Scanning the first FOV in X and Y axes scans both tilt and azimuth angles.

BSE emitted from the first sample are detected (204). The BSE may be detected using one or more detectors of the charged particle beam apparatus.

A first image of the first FOV is created based on the detected BSE (206).

A first area within the first image is identified where signals from the BSE are lower than other areas of the first image (208). The signals from the BSE are lower in areas where tilt and azimuth angles of the beam are substantially aligned with a crystal orientation of the crystalline material. In some embodiments, the tilt and azimuth angles of the charged particle beam used to scan the first area may be determined (210). In other embodiments, the tilt and azimuth angles are not directly determined. Instead, the deflections of the charged particle beam used to scan the first area may be determined. The deflections provide an indirection measure of the tilt and azimuth angles.

The method also involves scanning a second sample of the crystalline material (212). The second sample has a crystalline orientation relative to the charged particle beam apparatus that is substantially the same as the first sample. A second FOV used to scan the second sample is smaller than the first FOV used to scan the first sample, and the second FOV is scanned with approximately the same tilt and azimuth angles that were used to scan the first area of the first sample. In accordance with an embodiment, the second FOV is approximately centered with regard to the first area within the first image.

BSE emitted from the second sample are detected (214), and a second image of the second sample is created based on the detected BSE (216).

Crystal defects are identified within the second sample of the crystalline material (218). The defects are identified by areas within the second image where signals from the BSE are different (e.g., higher or lower) than other areas of the second image.

In this embodiment, the first area within the first image is identified as one where signals from the BSE are lower than other areas of the first image. This is an indication that the tilt angles used to scan the first area are substantially aligned with the crystal orientation so that there are fewer collisions between the charged particle beam and the crystalline material. Scanning the crystalline material a second time using these tilt angles allows defects to be identified because they produce BSE signals that are different than areas without defects.

It should be appreciated that the first sample and the second sample may be the same sample, or they may be different samples of the same crystalline material. In either case, crystal orientations of the first sample and the second sample are substantially the same with regard to the charged particle beam apparatus. This ensures that tilt angles that are substantially aligned with the first sample will be similarly aligned with the second sample.

When scanning the first sample, a relatively large FOV is scanned so that a relatively large range of tilt angles can be used. A large range of tilt angles increases the chance of identifying one or more smaller ranges of tilt angles that align with the crystal orientation. Once a smaller range of tilt angles that are substantially aligned with the crystal orientation are identified, a smaller FOV is scanned using the identified tilt angles.

A size of the smaller FOV may be determined based on the range of identified tilt angles. Alternatively, the size of the smaller FOV may be selected so that the smaller range of tilt angles are all substantially aligned with the crystal orientation. Substantially aligned in this context may be determined based on the signals from BSE that are detected during the scan. The signals from the BSE that are detected should provide resolution between areas that do not have crystal defects and those areas that do have crystal defects. If the smaller FOV is too large, at least some of the tilt angles will not be aligned with the crystal orientation and the BSE signals will not provide sufficient resolution to identify the crystal defects.

The process of scanning a large FOV using a relatively large range of tilt angles is illustrated in FIGS. 3A-3C and 4A-4C. It should be appreciated that any method or structure that can be used to change the tilt of a charged particle beam may be used with the embodiments described herein. FIGS. 3A-3C and 4A-4C are provided merely as examples.

Figure 3A:
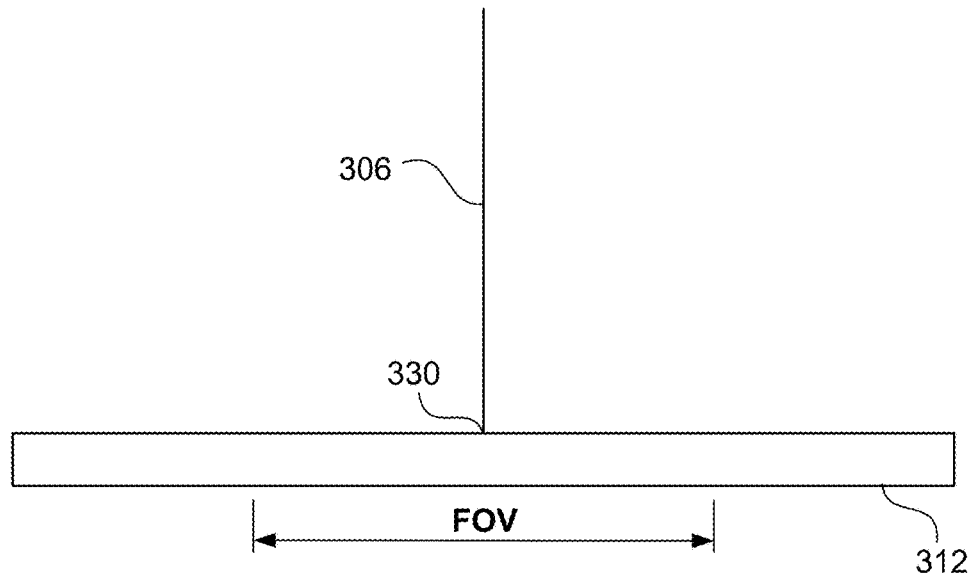
FIGS. 3A-3C are simplified cross-sectional views showing how tilt of a charged particle beam can be changed electronically to scan a FOV on a sample in accordance with some embodiments.
Figure 3B:
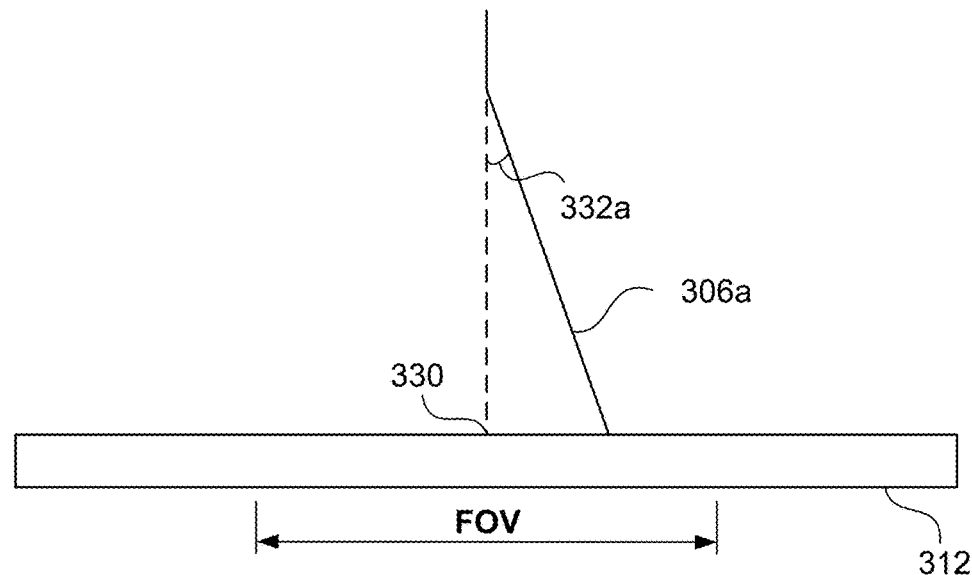
Figure 3C:
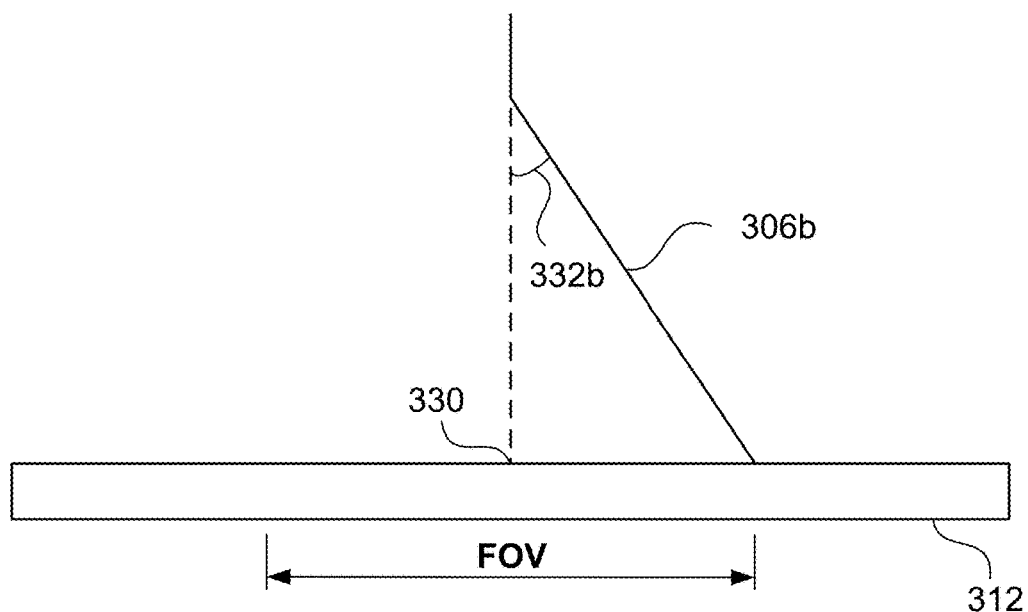

FIGS. 3A-3C are simplified cross-sectional views showing how tilt of a charged particle beam can be changed electronically to scan a FOV on a sample in accordance with some embodiments. FIG. 3A shows a charged particle beam 306 having approximately zero tilt that impinges on a center 330 of a FOV of sample 312.

FIG. 3B shows a deflected charged particle beam 306a that impinges on the sample 312 at a point that is to the right of the center 330 but still within the FOV. In this case the deflected charged particle beam 306a is tilted at an angle 332a.

FIG. 3C shows a deflected charged particle beam 306b that impinges on the sample 312 at a point that is to the right of the center 330 and at an edge of the FOV. In this case the deflected charged particle beam 306b is tilted at a larger angle 332b than the charged particle beam 306a. The beam in these figures may be tilted electronically using a deflection system that includes magnetic and/or electrostatic elements in accordance with known techniques.

FIGS. 3A-3C show that the tilt angle can be increased with distance from the center 330 of the FOV. In other embodiments, a zero tilt point may be positioned elsewhere within the FOV such as at an edge or corner. In yet other embodiments, all of the tilt angles used while scanning the FOV may be non-zero. In any case, the relatively large FOV is scanned using a relatively large range of tilt angles so that a range of tilt angles that are substantially aligned with the crystal orientation can be identified. The angles that are substantially aligned with the crystal orientation are identified by areas of the FOV where signals from the BSE are lower than other areas. If the resulting image does not include any areas where signals from the BSE are lower, a larger range of tilt angles and/or different tilt angles may be used until at least one area is identified.

Figure 4A:
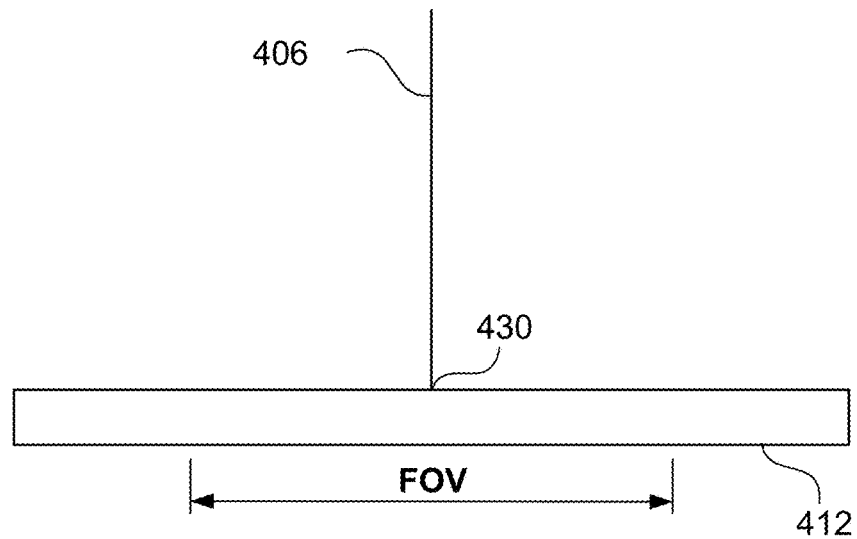
FIGS. 4A-4C are simplified cross-sectional views showing how tilt of a charged particle beam can be changed mechanically to scan a FOV on a sample in accordance with some embodiments.
Figure 4B:
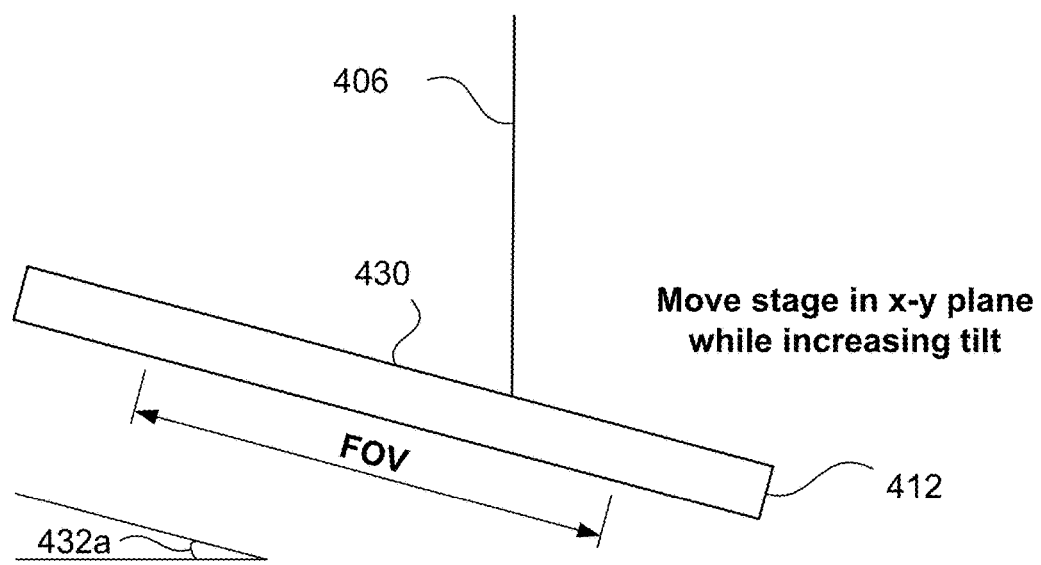
Figure 4C:
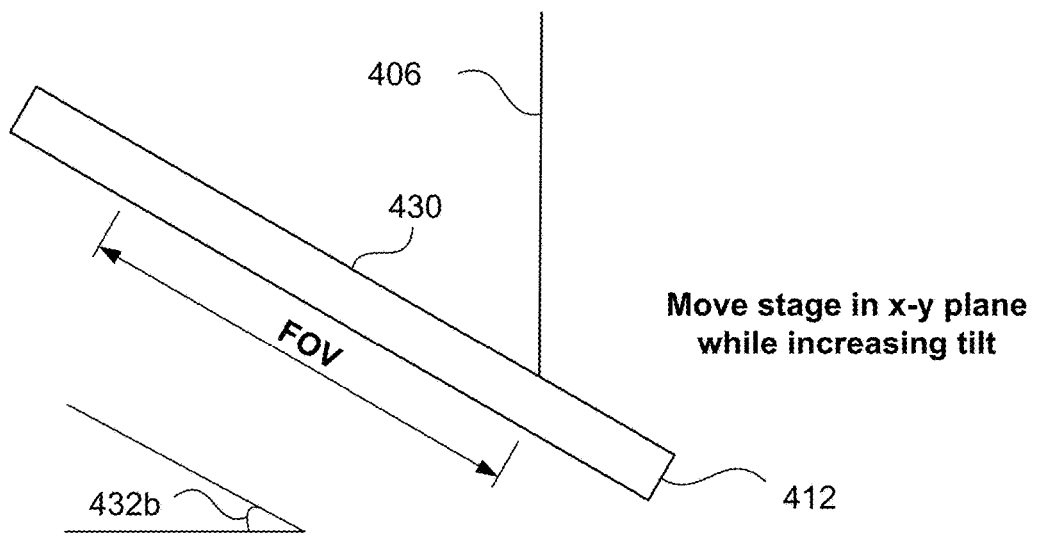

FIGS. 4A-4C are simplified cross-sectional views showing how tilt of a charged particle beam can be changed mechanically to scan a FOV on a sample in accordance with some embodiments. FIG. 4A shows a charged particle beam 406 having approximately zero tilt that impinges on a center 430 of a FOV of sample 412.

FIG. 4B shows that the sample 412 has been moved to the left relative to the charged particle beam 406 and tilted by an angle 432a. The tilt angle is changed in this example by tilting the sample without tilting the charged particle beam 406. After moving and tilting the sample, the charged particle beam 406 impinges on the sample 412 at a point that is to the right of the center 430 but still within the FOV.

FIG. 4C shows that the sample 412 has been moved further to the left compared to FIG. 4B and tilted by a larger angle 432b. After moving and tilting the sample, the charged particle beam 406 impinges on the sample 412 at a point that is to the right of the center 430 and at an edge of the FOV. The beam in this example is tilted mechanically by moving and tilting the sample 412 (or a stage supporting the sample). In other embodiments, the beam may be tilted by moving and tilting the column and/or by moving and tilting the sample and the column. In yet other embodiments, the beam may be tilted both electronically and mechanically.

Like FIGS. 3A-3C, FIGS. 4A-4C show that the tilt angle can be increased with distance from the center 430 of the FOV. As described above, a zero tilt point may be positioned elsewhere within the FOV or all of the tilt angles may be non-zero. After scanning the large FOV, the angles that are substantially aligned with the crystal orientation are identified by areas of the FOV where signals from the BSE are lower than other areas.

FIGS. 3A-3C and 4A-4C each capture three points as a charged particle beam is scanned across a FOV. These figures are not intended to imply that scanning is performed from a center outward or that scanning is not continuous. Rather, they are intended to show how a FOV can be scanned using a plurality of different tilt angles of a charged particle beam.

Figure 5:
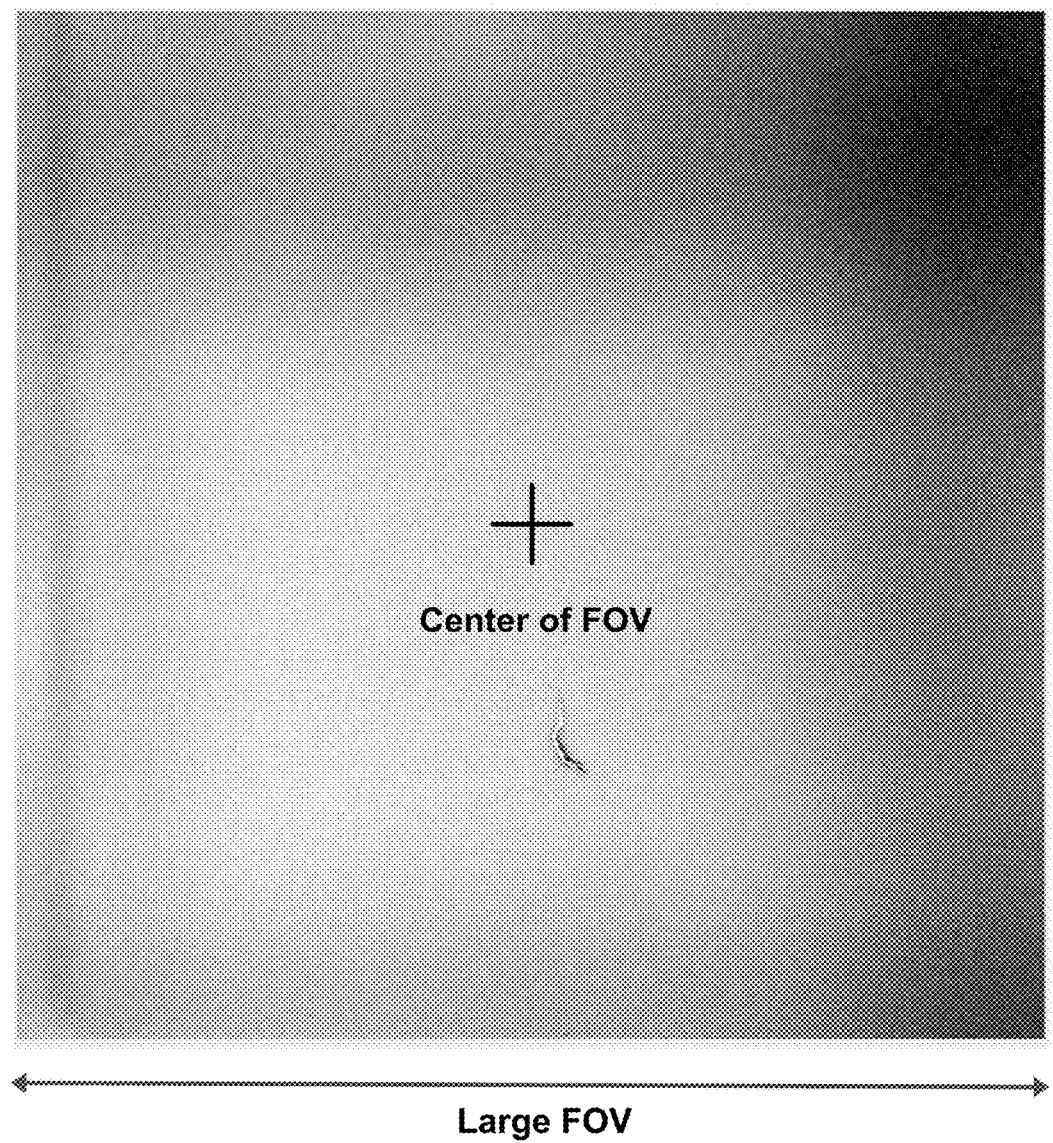
FIG. 5 is an image from a scan over a large FOV of a crystalline material showing areas where signals from BSE are lower than other areas of the image in accordance with some embodiments.

FIG. 5 is an image from a scan over a large FOV of a crystalline material showing areas where signals from BSE are lower than other areas of the image in accordance with some embodiments. A center of the image (or center of the FOV) is marked for reference. Note that the squiggly line just below the center is merely an artifact of the imaging or displaying process. In some embodiments, the charged particle beam has approximately zero tilt at the center. In this image, lighter areas correspond to areas where signals from the BSE are higher (or more BSE), and darker areas correspond to areas where signals from the BSE are lower (or fewer BSE).

In this example, an area in the upper right corner of FIG. 5 may be identified as having lower BSE signals than other areas of the image. This indicates that the tilt angles used to scan this area are substantially aligned with the crystal orientation. This area is darker and larger than other areas where signals from the BSE are also lower.

Because the tilt angles change as the FOV is scanned, there were likely a number of different tilt angles used to scan the darker area in the upper right corner of FIG. 5. This range of tilt angles may be selected as being substantially aligned with the crystal orientation of the material. Referring back to Step 210 of FIG. 2, the identified tilt angles or the deflection used in the darker area may be used to scan and identify crystal defects in a second sample. Alternatively, a slightly larger or smaller ranges of tilt angles may be used.

Figure 6A:
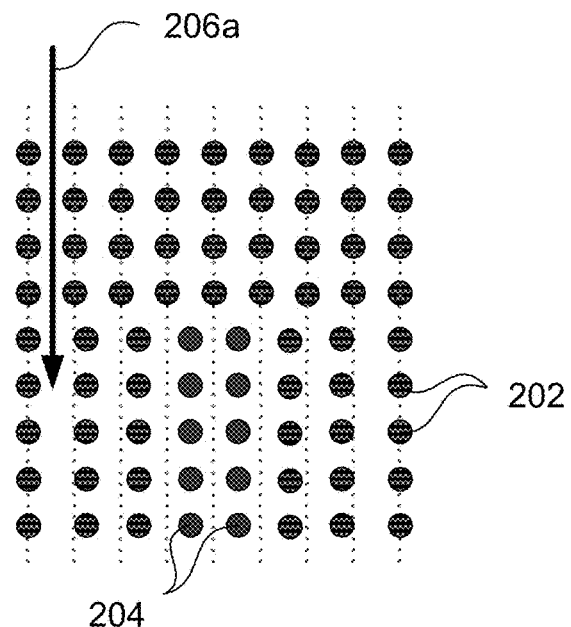
FIGS. 6A-6C are simplified cross-sectional views showing a charged particle beam substantially aligned with a crystalline structure in accordance with some embodiments.
Figure 6B:
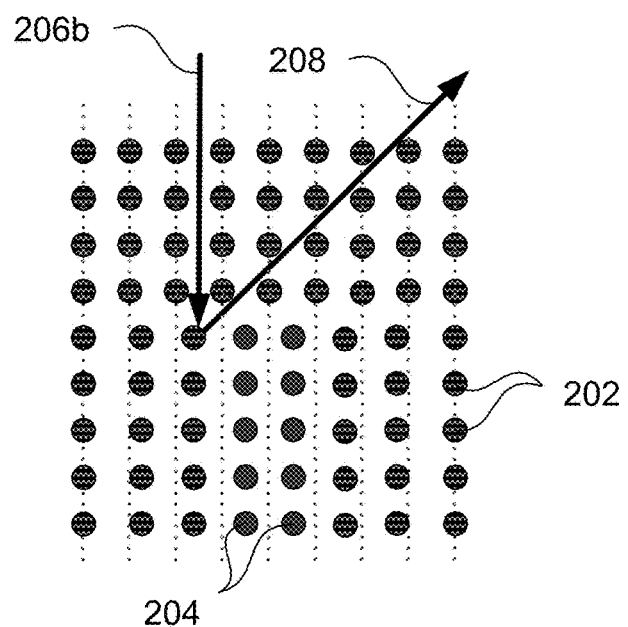
Figure 6C:
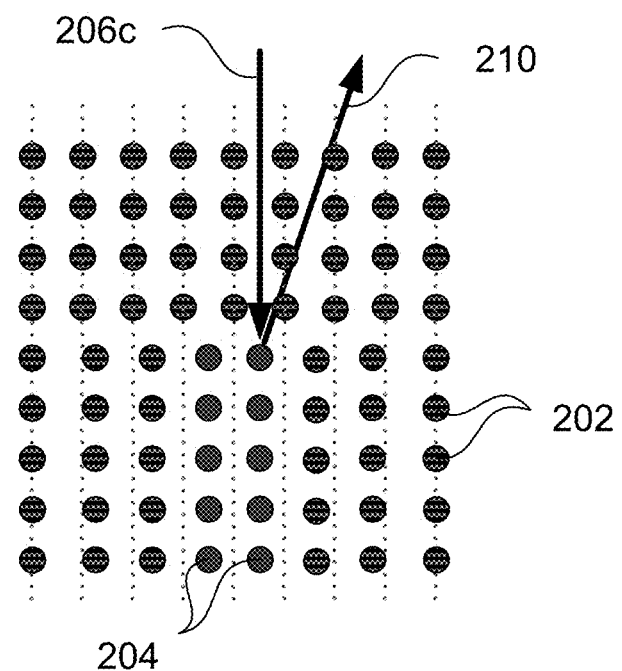

FIGS. 6A-6C are simplified cross-sectional views showing a charged particle beam substantially aligned with a crystalline structure in accordance with some embodiments. These figures provide insight into how a charged particle beam apparatus using tilt angles that are substantially aligned with the crystalline structure may be used to detect crystal defects.

FIG. 6A shows a charged particle beam 206a that is substantially aligned with a crystalline structure of atoms or molecules 202. In this example, the crystalline structure also includes defects formed by foreign atoms or molecules 204. Because the charged particle beam 206a is substantially aligned with the crystalline structure, it travels through the material with a minimal number of collisions. As a result, signals from BSE will be lower than when the beam is not aligned with the crystalline structure.

FIG. 6B shows a charged particle beam 206b that is still substantially aligned with the crystalline structure, but it collides with one of the atoms or molecules 202 of the crystalline structure that is slightly out of place due to the foreign atoms or molecules 204. The atoms or molecules 202 are only slightly out of place in this example, so the collision is a glancing collision that produces primarily SE. Thus, signals from BSE may still be relatively low.

FIG. 6C shows a charged particle beam 206c that is still substantially aligned with the crystalline structure, but it collides with one of the foreign atoms or molecules 204. In this example, the foreign atom or molecule fills an area of the crystalline structure that would normally be vacant. The collision in this example is a direct collision that is likely to produce BSE. Thus, signals from the BSE may be higher than the scenarios shown in FIGS. 6A-6B indicating a crystal defect.

Although not specifically shown in these figures, vacancies are another form of crystal defect. Vacancies result when atoms or molecules are missing from a crystalline structure. A charged particle beam that is substantially aligned with a crystalline structure produces fewer BSE when scanning an area with one or more vacancies. Signals from the BSE may be lower in this instance. Thus, defects may be detected when signals from the BSE are higher or lower than other areas of the second image.

Figure 7:
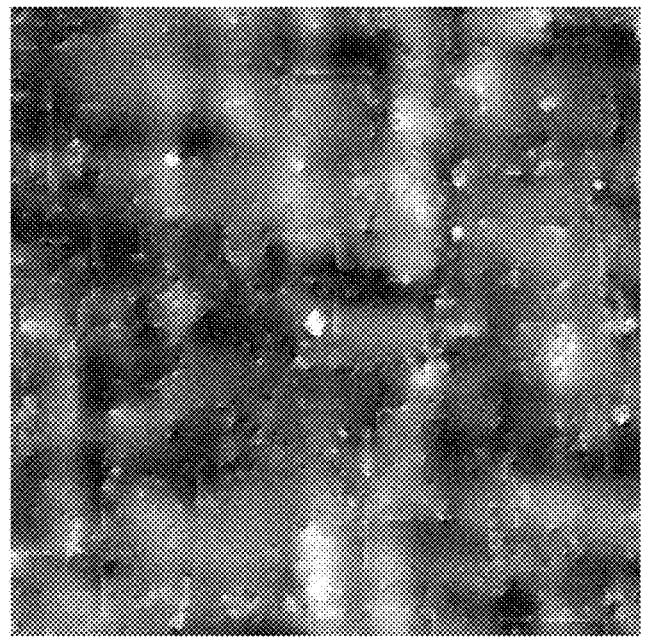
FIGS. 7-8 are SEM images showing defects identified by areas of the images where signals from the BSE are different than other areas in accordance with some embodiments.
Figure 8:
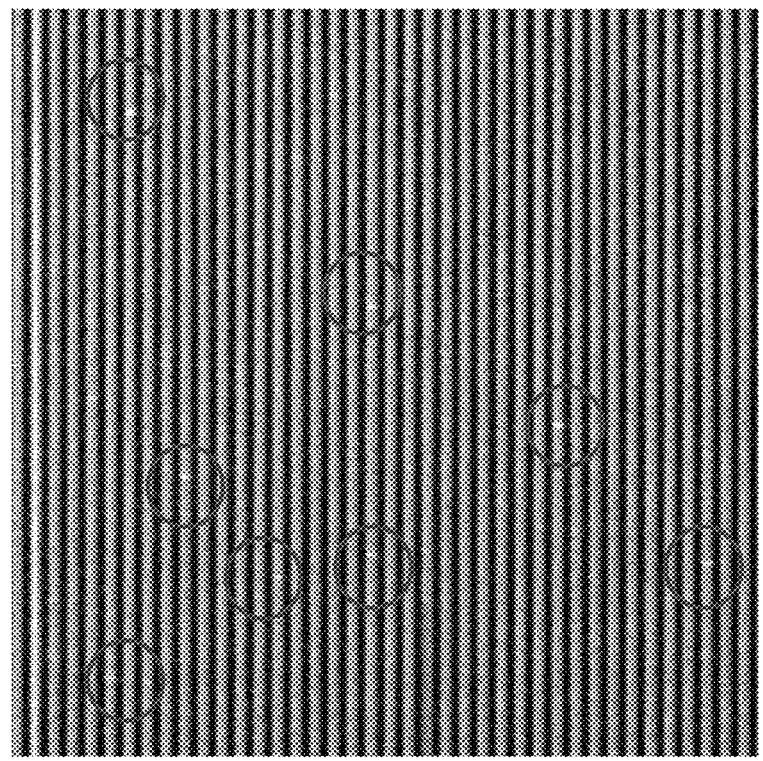

FIGS. 7-8 are SEM images showing defects identified by areas of the images where signals from the BSE are different than other areas of the images in accordance with some embodiments. These images were obtained using methods described herein. FIG. 7 shows defects in an un-patterned crystalline material, while FIG. 8 shows defects in a patterned crystalline material. In FIG. 8 the defects are manifested as small horizontal lines on the patterned structures that are brighter than adjacent portions of the structures.

Figure 9:
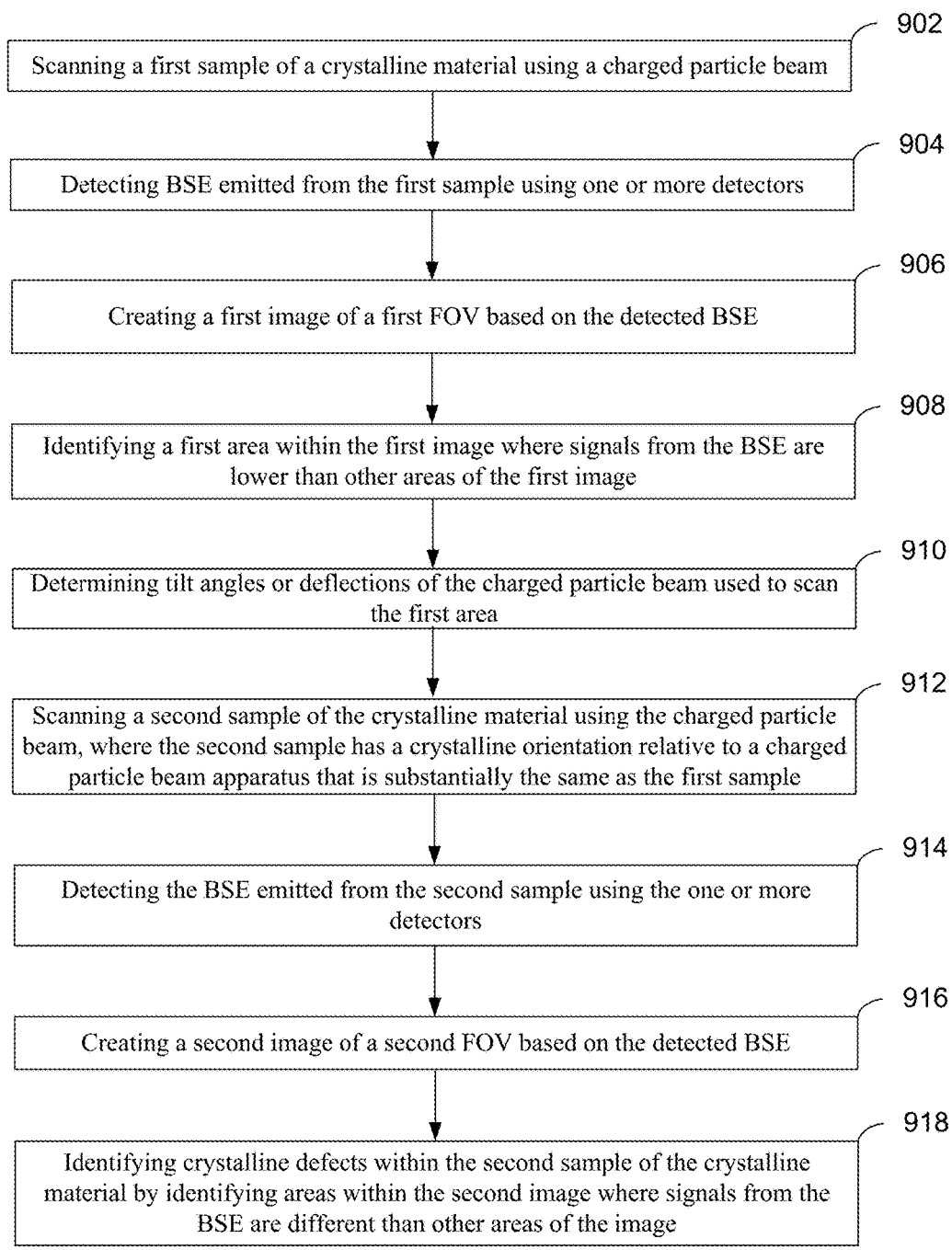
FIGS. 9-10 are flowcharts of methods for detecting defects in crystalline materials in accordance with some embodiments.

FIG. 9 is a flowchart of a method for detecting defects in crystalline materials in accordance with an embodiment. The method involves scanning a first sample of a crystalline material using a charged particle beam (902). The charged particle beam may have a beam energy of at least 2 kV or 3 kV or more to increase probability of generating BSE. In an embodiment, a first FOV of the charged particle beam may cover an area of at least 100 µm by 100 µm or greater on the first sample of the crystalline material. In another embodiment, a first FOV of the charged particle beam may cover an area of at least 50 µm by 50 µm or greater on the first sample of the crystalline material. The charged particle beam may have approximately zero tilt at a center of the first FOV, and a tilt angle of the charged particle beam may increase with distance from the center of the first FOV. This provides for a number of different tilt angles to be used during the scan. In some embodiments, the different tilt angles may extend from 0° to as high as 15° or more relative to a surface of the sample. The angles are typically measured with regard to a surface of a sample. Azimuth angles may vary from 0° to 360°.

BSE emitted from the first sample are detected using one or more detectors (904).

A first image of the first FOV is created based on the detected BSE (906).

A first area within the first image is identified where signals from the BSE are lower than other areas of the first image (908). The signals from the BSE are lower in areas where the tilt angles of the charged particle beam are substantially aligned with a crystal orientation of the crystalline material. In some embodiments, the first image may include multiple areas where signals from the BSE are lower than other areas of the first image, and identifying the first area within the first image may include identifying an area where signals from the BSE are lower than any other areas of the first image. In other embodiments, identifying the first area within the first image may include identifying an area where signals from the BSE are lower than other areas of the first image and where the first area is larger than the other areas of the first image. In yet other embodiments, identifying the first area within the first image may include identifying an area within the first image that is darker than other areas of the first image. The first area may be identified automatically using known image processing techniques.

The tilt angles of the charged particle beam or the deflections of the charged particle beam used to scan the first area are determined (910).

The method also involves scanning a second sample of the crystalline material using the charged particle beam, where the second sample has a crystalline orientation relative to the charged particle beam apparatus that is substantially the same as the first sample (912). As explained previously, the first sample and the second may be the same sample, or they may be different samples of the same crystalline material. The charged particle beam may have a beam energy of at least 2 kV or more to increase probability of generating BSE. The charged particle beam may have approximately the same tilt angles or deflections as those used to scan the first area. A second FOV of the charged particle beam may cover an area of no more than 50 µm by 50 µm on the second sample of the crystalline material in some embodiments.

BSE emitted from the second sample are detected using one or more detectors (914).

A second image of the second FOV is created based on the detected BSE (916).

Crystal defects are identified within the second sample of the crystalline material by identifying areas within the second image where signals from the BSE are different than other areas of the second image (918).

In some embodiments, the first sample of the crystalline material and the second sample of the crystalline material are stationary relative to the charged particle beam apparatus during scanning. In these embodiments, the tilt angle of the charged particle beam may be changed electronically and/or the column may be tilted. In other embodiments, the first sample of the crystalline material and the second sample of the crystalline material may be moved relative to the charged particle beam apparatus during scanning. In these embodiments, the tilt angle of the charged particle beam may be changed mechanically.

Figure 10:
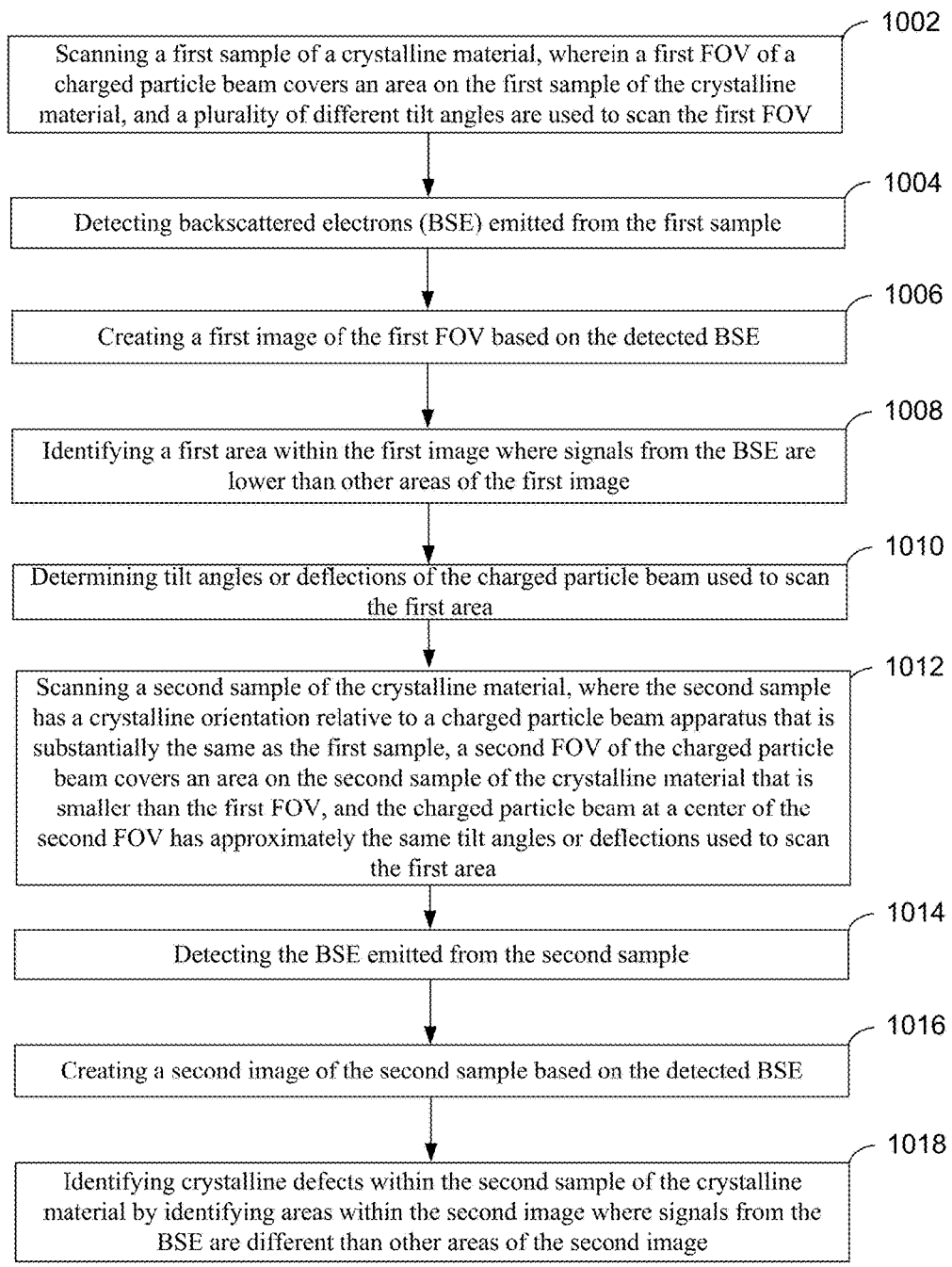

FIG. 10 is a flowchart of a method for detecting defects in crystalline materials in accordance with another embodiment. The method involves scanning a first sample of a crystalline material, where a first FOV of a charged particle beam covers an area on the first sample of the crystalline material, and a plurality of different tilt angles are used to scan the first FOV (1002). In some embodiments, the charged particle beam may have a beam energy of at least 2 kV or more, a first FOV of the charged particle beam may cover an area of at least 100 µm by 100 µm or greater on the first sample of the crystalline material, the charged particle beam may have approximately zero tilt at a center of the first FOV, and/or a tilt angle of the charged particle beam may increase with distance from the center of the first FOV.

BSE emitted from the first sample are detected (1004).

A first image of the first FOV is created based on the detected BSE (1006).

A first area within the first image is identified where signals from the BSE are lower than other areas of the first image (1008). The first area may be identified automatically using known image processing techniques.

The tilt angles or deflections of the charged particle beam used to scan the first area are determined (1010).

The method also involves scanning a second sample of the crystalline material using the charged particle beam, where the second sample has a crystalline orientation relative to the charged particle beam apparatus that is substantially the same as the first sample, a second FOV of the charged particle beam covers an area on the second sample of the crystalline material that is smaller than the first FOV, and the charged particle beam has approximately the same tilt angles or deflections as those used to scan the first area (1012). As explained previously, the first sample and the second may be the same sample, or they may be different samples of the same crystalline material. In some embodiments, the charged particle beam may have a beam energy of at least 2 kV or more and/or a second FOV of the charged particle beam may cover an area of no more than 50 μm by 50 μm on the second sample of the crystalline material.

BSE emitted from the second sample are detected (1014).

A second image of the second FOV is created based on the detected BSE (1016).

Crystal defects are identified within the second sample of the crystalline material by identifying areas within the second image where signals from the BSE are different than other areas of the second image (1018).

It should be appreciated that the specific steps illustrated in FIGS. 9-10 provide particular methods according to some embodiments. Other sequences of steps may also be performed according to alternative embodiments. For example, alternative embodiments may perform some of the steps outlined above in a different order. Moreover, the individual steps outlined in FIGS. 9-10 may include multiple sub-steps that may be performed in various sequences. Furthermore, additional steps may be added or removed depending on the particular application.

In the above examples, crystal defects are identified by scanning a sample using tilt angles that are substantially aligned with a crystal orientation of a crystalline material. The tilt angles are determined from a previous scan of a larger FOV. In some embodiments, the crystal defects are identified by scanning a smaller FOV using a smaller range of tilt angles. The tilt angles used to identify the crystal defects in some embodiments may extend, for example, over a range on the order of about 1°. The range of tilt angles may be higher or lower in other embodiments. Because a range of tilt angles is used, sensitivity to different crystal defects may vary across the smaller FOV and/or overall sensitivity may vary. In some embodiments, at least some areas within the smaller FOV may be scanned multiple times using different tilt angles. This can improve sensitivity in some situations by providing information for a particular area from different tilt angles. This can be achieved, for example, by performing overlapping scans where the overlapping areas are scanned using different tilt angles. The information from different tilt angles is also helpful in classifying the defects based on shape, intensity, grey level, structural orientation, or the like. The information from different tilt angles may also be helpful in differentiating between bulk, surface, and/or interface crystal defects.

In embodiments where the crystalline material is patterned, different structures or areas within a structure may be identified that provide improved sensitivity to crystal defects, improved sensitivity to particular types of defects, and/or better correlation to a particular process or characteristic (e.g., layer thickness). These locations may be identified empirically or based on known design and process interactions.

In some embodiments, test structures may be formed near actual structures to provide an area for analysis (e.g., in locations on a wafer such as between dies (scribe-lines), within the dies, or the like). Test structures may be formed to exploit known structural, design, and/or process interactions or sensitivities. Test structures may include, for example, structures of variable pitch and 1D/2D layouts.

In some embodiments, the methods described herein may be used for process monitoring and/or control. For example, the methods may be used to identify crystal defects in a substrate of crystalline material or in layers of crystalline material that are deposited on a substrate. The methods may also be used to identify the impact of a particular process on crystal defects in the substrate or in the deposited layers. Non-limiting examples of crystalline materials that may be analyzed using embodiments described herein include silicon, silicon germanium (SiGe), germanium (Ge), group III-V compound materials, group II-VI compound materials, ternary (e.g., InGaAs) and quaternary (e.g., InGaAsP) compound materials, and the like. Non-limiting examples of processes that may be monitored and/or controlled using embodiments described herein include deposition, implant, anneal, chemical mechanical planarization (CMP), etch, and the like.

Some embodiments may automatically detect, count, measure, and/or classify the crystal defects using image processing techniques. Some embodiments may also identify areas of an image where the charged particle beam is substantially aligned with a crystal orientation.

These areas may be identified based on signal-to-noise ratio (SNR).

Results such as counts, densities, or the like can be provided based on FOV, area, structure, location, die, and/or wafer. Results may also be provided based on comparisons (FOV-to-FOV, area-to-area, etc.). In some embodiments, the crystal defects may be identified and/or classified based on their characteristic shape, intensity, size (length and/or width), grey level, orientation, and/or other characteristics. This enables statistical analysis of distribution and clustering into different defect types, sources, and criticality.

While the foregoing is directed to specific embodiments, other and further embodiments may be devised without departing from the basic scope thereof, and the scope thereof is determined by the claims that follow.

What is claimed is:

1. A method for detecting defects in a crystalline material using a charged particle beam apparatus, the method comprising:
    scanning a first sample of the crystalline material using a charged particle beam, wherein:
        the charged particle beam has a beam energy of at least 2 kV,
        a first field of view (FOV) of the charged particle beam covers an area of at least 50 μm by 50 μm on the first sample of the crystalline material,
        the charged particle beam has approximately zero tilt at a center of the first FOV, and
        the charged particle beam has an increasing tilt angle with distance from the center of the first FOV;
    detecting backscattered electrons (BSE) emitted from the first sample of the crystalline material using one or more detectors of the charged particle beam apparatus;
    creating a first image of the first FOV based on the detected BSE;
    identifying a first area within the first image where signals from the BSE are lower than other areas of the first image; and thereafter
    scanning a second sample of the crystalline material using the charged particle beam, the second sample having a crystalline orientation relative to the charged particle beam apparatus that is substantially the same as the first sample, wherein:

the charged particle beam has the beam energy of at least 2 kV, a second FOV of the charged particle beam covers an area of no more than 50 µm by 50 µm on the second sample of the crystalline material, and the charged particle beam has approximately the same tilt angles or deflections as those used to scan the first area, detecting the BSE emitted from the second sample of the crystalline material using the one or more detectors of the charged particle beam apparatus;

creating a second image of the second FOV based on the detected BSE; and identifying crystal defects within the second sample of the crystalline material by identifying areas within the second image where signals from the BSE are different than other areas of the second image.

2. The method of claim 1 wherein the first image includes multiple areas where signals from the BSE are lower than other areas of the first image, and identifying the first area within the first image includes identifying an area where signals from the BSE are lower than any other areas of the first image.

3. The method of claim 1 wherein tilt angles of the charged particle beam are changed electronically while scanning the first FOV and while scanning the second FOV.

4. The method of claim 1 wherein identifying the first area within the first image includes identifying an area within the first image that is darker than other areas of the first image.

5. The method of claim 1 wherein the first sample of the crystalline material and the second sample of the crystalline material are stationary relative to the charged particle beam apparatus during scanning.

6. A method for detecting defects in a crystalline material using a charged particle beam apparatus, the method comprising:

scanning a first sample of the crystalline material using a charged particle beam, wherein a first field of view (FOV) of the charged particle beam covers an area on the first sample of the crystalline material, and a plurality of different tilt angles of the charged particle beam are used to scan the first FOV;

detecting backscattered electrons (BSE) emitted from the first sample of the crystalline material using one or more detectors of the charged particle beam apparatus;

creating a first image of the first FOV based on the detected BSE;

identifying a first area within the first image where signals from the BSE are lower than other areas of the first image; and thereafter scanning a second sample of the crystalline material using the charged particle beam, the second sample having a crystalline orientation relative to the charged particle beam apparatus that is substantially the same as the first sample, wherein a second FOV of the charged particle beam covers an area on the second sample of the crystalline material that is smaller than the first FOV, and the charged particle beam has approximately the same tilt angles or deflections as those used to scan the first area;

detecting the BSE emitted from the second sample of the crystalline material using the one or more detectors of the charged particle beam apparatus;

creating a second image of the second FOV based on the detected BSE; and identifying crystal defects within the second sample of the crystalline material by identifying areas within the second image where signals from the BSE are different than other areas of the second image.

7. The method of claim 6 wherein the charged particle beam has a beam energy of at least 2 kV.

8. The method of claim 6 wherein the area of the first FOV on the first sample of the crystalline material is at least 100 µm by 100 µm, and the area of the second FOV on the second sample of the crystalline material is no more than 50 µm by 50 µm.

9. The method of claim 6 wherein the charged particle beam has an approximately zero tilt at a center of the first FOV, and the charged particle beam has an increasing tilt angle with distance from the center of the first FOV.

10. The method of claim 6 wherein the first image includes multiple areas where signals from the BSE are lower than other areas of the first image, and identifying the first area within the first image includes identifying an area where signals from the BSE are lower than any other areas of the first image.

11. The method of claim 6 wherein tilt angles of the charged particle beam are changed electronically while scanning the first FOV and while scanning the second FOV.

12. The method of claim 6 wherein identifying the first area within the first image includes identifying an area within the first image that is darker than other areas of the first image.

13. A nontransitory computer-readable medium storing instructions that, when executed by one or more processors of a charged particle beam apparatus, cause the charged particle beam apparatus to perform operations comprising:

scanning a first sample of crystalline material using a charged particle beam, wherein a first field of view (FOV) of the charged particle beam covers an area on the first sample of the crystalline material, and a plurality of different tilt angles of the charged particle beam are used to scan the first FOV;

detecting backscattered electrons (BSE) emitted from the first sample of the crystalline material using one or more detectors of the charged particle beam apparatus;

creating a first image of the first FOV based on the detected BSE;

scanning a second sample of the crystalline material using the charged particle beam, wherein a second FOV of the charged particle beam covers an area on the second sample of the crystalline material, and the charged particle beam has the same tilt angles or deflections as those used to scan a first area within the first image where signals from the BSE are lower than other areas of the first image;

detecting the BSE emitted from the second sample of the crystalline material using the one or more detectors of the charged particle beam apparatus; and creating a second image of the second FOV based on the detected BSE.

14. The nontransitory computer-readable medium of claim 13 further comprising instructions that, when executed by the one or more processors, cause the charged particle beam apparatus to perform operations comprising:

identifying the first area within the first image using an image processing technique; and determining the tilt angles or deflections of the charged particle beam used to scan the first area.

15. The nontransitory computer-readable medium of claim 13 further comprising instructions that, when executed by the one or more processors, cause the charged particle beam apparatus to perform operations comprising identifying crystal defects within the second sample of the crystalline material by identifying areas within the second image where signals from the BSE are different than other areas of the second image.

16. The nontransitory computer-readable medium of claim 13 wherein the area of the first FOV on the first sample of the crystalline material is at least 100 µm by 100 µm, and the area of the second FOV on the second sample of the crystalline material is no more than 50 µm by 50 µm.

17. The nontransitory computer-readable medium of claim 13 wherein the charged particle beam has an approximately zero tilt at a center of the first FOV, and the charged particle beam has an increasing tilt angle with distance from the center of the first FOV.

18. The nontransitory computer-readable medium of claim 13 wherein the first image includes multiple areas where signals from the BSE are lower than other areas of the first image, and identifying the first area within the first image includes identifying an area where signals from the BSE are lower than any other areas of the first image.

19. The nontransitory computer-readable medium of claim 13 wherein tilt angles of the charged particle beam are changed electronically while scanning the first FOV and while scanning the second FOV.

20. The nontransitory computer-readable medium of claim 13 wherein identifying the first area within the first image includes identifying an area within the first image that is darker than other areas of the first image.

* * * * *